United States Patent [19]

Bernasconi et al.

[11] 4,260,779

[45] Apr. 7, 1981

[54] OXOTHIA COMPOUNDS

[75] Inventors: Raymond Bernasconi, Oberwil; Pier G. Ferrini, Binningen; Richard Göschke, Bottmingen; Jacques Gosteli, Basel, all of Switzerland

[73] Assignee: Ciba-Geigy Corporation, Ardsley, N.Y.

[21] Appl. No.: 92,821

[22] Filed: Nov. 9, 1979

Related U.S. Application Data

[63] Continuation of Ser. No. 780,951, Mar. 24, 1977, abandoned.

[30] Foreign Application Priority Data

Apr. 9, 1976 [CH] Switzerland ............... 4538/76

[51] Int. Cl.³ ............................................ C07D 333/64
[52] U.S. Cl. ........................................ 549/52; 424/263; 424/270; 424/272; 424/275; 544/204; 544/214; 544/236; 544/240; 546/274; 549/54; 549/55
[58] Field of Search ............... 549/33, 52, 55, 54; 546/274

[56] References Cited

U.S. PATENT DOCUMENTS

| | | | |
|---|---|---|---|
| 3,413,308 | 11/1968 | Bockstahler | 260/330.5 |
| 3,655,693 | 4/1972 | Shen et al. | 260/332.2 C |
| 3,971,814 | 7/1976 | Stoss et al. | 260/330.5 |

FOREIGN PATENT DOCUMENTS 2713684  10/1977  Fed. Rep. of Germany ......... 546/274

OTHER PUBLICATIONS

Kadin, J. Med. Chem. vol. 13, pp. 551–552 (1972).
Burger, Medicinal Chemistry, 2nd Ed., pp. 79–81, Interscience Publishers Inc. NY (1960).
Chemical Abstracts, vol. 88, abst. No. 88: 37601q (p. 484) (1978) (abst. of Ger. Offen. No. 2,713,584 pub. 10/20/77).

*Primary Examiner*—John D. Randolph
*Attorney, Agent, or Firm*—Prabodh I. Almaula

[57] ABSTRACT

Oxothia compounds, especially 2-oxo-2,3-dihydro-benzo[b]thiophene compounds of the formula

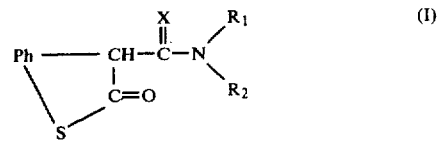

in which Ph represents an optionally substituted 1,2-phenylene radical, X represents oxygen or sulphur, $R_1$ represents an organic radical bonded via a carbon atom and $R_2$ denotes hydrogen or an optionally substituted hydrocarbon radical of aliphatic character, and their salts are useful as peripheral analgetics and/or as antiphlogistic uricosuric and/or thrombolytic agents.

9 Claims, No Drawings

OXOTHIA COMPOUNDS

This is a continuation of application Ser. No. 780,951 filed on Mar. 24, 1977, now abandoned.

The invention relates to oxothia compounds, especially 2-oxo-2,3-dihydro-benzo[b]thiophene compounds of the formula

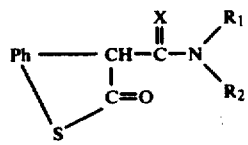

in which Ph represents an optionally substituted 1,2-phenylene radical, X represents oxygen or sulphur, $R_1$ represents an organic radical bonded via a carbon atom and $R_2$ denotes hydrogen or an optionally substituted hydrocarbon radical of aliphatic character, and their salts as well as processes for their preparation and also pharmaceutical formulations which contain compounds of the formula I or salts thereof, and the use of such compounds.

The above 2-oxo-2,3-dihydro-benzo[b]thiophene compounds can also be in the tautomeric form, that is to say in the form of 2-hydroxy-benzo[b]thiophene compounds.

In the context of the present description, organic radicals and compounds designated as "lower" contain up to 7, and preferably up to 4, carbon atoms.

An organic radical bonded via a carbon atom is, for example, an optionally substituted hydrocarbon radical of aliphatic character, for example an aliphatic, cycloaliphatic, cycloaliphatic-aliphatic or araliphatic hydrocarbon radical, or, in particular, a hydrocarbon radical of aromatic character, that is to say an optionally substituted aromatic or heteroaromatic radical bonded via a carbon atom.

An aliphatic hydrocarbon radical is, in particular, lower alkyl, and also lower alkenyl or lower alkinyl, a cycloaliphatic hydrocarbon radical is, for example, cycloalkyl or cycloalkenyl, preferably with up to 8 ring members, and a cycloaliphatic-aliphatic hydrocarbon radical is, for example, cycloalkyl-lower alkyl, preferably with up to 8 ring members in the cycloaliphatic part, whilst an araliphatic hydrocarbon radical is, in particular, monocyclic aryl-lower alkyl, that is to say phenyl-lower alkyl. An aromatic hydrocarbon radical is, above all, monocyclic aryl, that is to say phenyl.

A hetero-aromatic radical is, in particular, a monocyclic hetero-aromatic radical with 5 or 6 ring members and at least one ring member is a hetero atom, for example a nitrogen, oxygen or sulphur atom.

Substituents of the abovementioned organic radicals, and especially of an aromatic or hetero-aromatic $R_1$, and also of the 1,2-phenylene radical Ph, are, inter alia, lower alkyl, lower alkoxy, lower-alkoxy carbonyl, carboxy, halogen, trifluoromethyl or nitro, and two adjacent carbon atoms, especially in a hetero-aromatic radical, can also be substituted by 1,3-butandien-1,4-ylene which is optionally substituted, for example like an aromatic radical, that is to say an aromatic radical being fused on and a bicyclic, and especially a benzohetero-aromatic radical, being formed.

Lower alkyl is, for example, methyl, ethyl, n-propyl, isopropyl, n-butyl or tert.-butyl, whilst lower alkenyl is, for example, allyl or methallyl, and lower alkinyl is, for example, propargyl.

Cycloalkyl is, for example, cyclopropyl, cyclopentyl, cyclohexyl or cycloheptyl and cycloalkenyl represents, for example, cyclopentenyl, cyclohexenyl or cycloheptenyl which contain the double bond in any suitable position, whilst cycloalkyl-lower alkyl represents, for example, cyclopropylmethyl, cyclopentylmethyl, cyclohexylmethyl or 2-cyclohexylethyl.

Phenyl-lower alkyl is, for example, benzyl or 1- or 2-phenylethyl.

A hetero-aromatic radical containing one hetero atom is, inter alia, monocyclic monoazaaryl, monooxaaryl or monothiaaryl, for example pyridyl, such as 2-, 3- or 4-pyridyl, furyl, such as 2-furyl, thienyl, such as 2-thienyl. A corresponding radical containing two ring hetero atoms is, inter alia, 6-membered monocyclic diazaaryl, for example pyridazinyl, such as 3- or 4-pyridazinyl, pyrimidinyl, such as 2- or 4pyrimidinyl, or pyrazinyl, such as 2-pyrazinyl, or 5-membered monocyclic oxazaaryl or thiazaaryl, such as oxazolyl, for example 2-oxazolyl, isoxazolyl, for example 3-isoxazolyl, thiazolyl, for example 2-thiazolyl, or isothiazolyl, for example 3-isothiazolyl. Corresponding hetero-aromatic radicals in which two adjacent ring carbon atoms are substituted by 1,3-butadien-1,4-ylene, that is to say benzohetero-aromatic radicals, are, inter alia, bicyclo benzoazaaryl, for example quinolinyl, such as 4-quinolinyl, or isoquinolinyl, or bicyclic benzoxazaaryl or benzothiazaaryl, for example benzoxazolyl, for example 2-benzoxazolyl, or benzthiazolyl, for example 2-benzthiazolyl.

Lower alkoxy is, for example, methoxy, ethoxy, n-propoxy, isopropoxy, n-butoxy or isobutoxy.

Halogen is, above all, halogen with an atomic number of up to 35, that is to say fluorine, chlorine or bromine.

Salts of compounds of the formula I are, above all, pharmaceutically usable salts with bases, and above all metal salts or ammonium salts. Metal salts are, above all, metal salts derived from metals of groups Ia, Ib, IIa and IIb of the periodic table of the elements, such as alkali metal salts or alkaline earth metal salts, for example sodium, potassium, magnesium, calcium, zinc or copper salts. Ammonium salts are, above all, salts with secondary or tertiary organic bases, for example with morpholine, thiomorpholine, piperidine, pyrrolidine, dimethylamine or diethylamine or triethylamine, but to a lesser extent also salts with ammonia. The formation of a salt with compounds of the formula I probably takes place from the tautomeric 2-hydroxy-benzo[b]thiophene form.

The new compounds display valuable pharmacological properties. Peripheral analgesic actions, which can be demonstrated both in mice, by the phenyl-p-benzoquinone writhing test, and in rats, by the acetic acid writhing test analogously to the method described by Krupp et al., Schweiz. med. Wsch., volume 105, page 646 (1975), with doses of about 1 to about 100 mg/kg administered perorally, are in the forefront of the spectrum of action. In addition the compounds display anti-inflammatory actions, which can be demonstrated, for example, by the kaolin oedema test in rats analogously to the method described by Menassé and Krupp, Toxicol. Appl. Pharmacol. volume 29, page 389 (1974), with doses of about 30 mg/kg to about 100 mg/kg administered perorally. In vitro, in doses of 0.1–50 μg/ml, these compounds also inhibit the prostaglandin-synthetase system to a noticeably great extent (method: White and Glassman, Prostaglandins, volume 7, No. 2, page 123 (1974)). Furthermore, they display uricosuric actions, which can be demonstrated, for example, by the phenol red excretion test analogously to the method described by Swingle et al., Arch. int. Pharmacodyn., volume 189, page 129 (1971), with doses of about 100 mg/kg administered perorally. The compounds are useful as peripheral analgesics, for example for the treatment of conditions of pain resulting from very diverse causes, or as antiphlogistic agents, for example for the treatment of arthritic inflammations, or for influencing traumatic inflammatory conditions and tumefacient conditions, and also as uricosuric agents, for example for the treatment of gout.

The new compounds also display antithrombotic actions, which can be demonstrated in rabbits in experimental pulmonary embolism, analogously to the method described by Silver et al., Science, volume 183, page 1,085 (1974), with doses of about 3 mg/kg to about 30 mg/kg administered perorally. The compounds are useful also as thrombolytic agents.

The invention relates above all to compounds of the formula I in which Ph represents 1,2-phenylene which is optionally substituted by lower alkyl, lower alkoxy, lower-alkoxy carbonyl, carboxy, halogen, trifluoromethyl and/or nitro, X represents oxygen or, to a lesser extent, represents sulphur, $R_1$ represents lower alkyl, lower alkenyl, cycloalkyl, cycloalkenyl or cycloalkyl-lower alkyl or a phenyl-lower alkyl, or above all, phenyl radical which are optionally substituted by lower alkyl, lower alkoxy, lower, alkoxy carbonyl, carboxy, halogen, trifluoromethyl and/or nitro, a 6-membered mono- or di-azaaryl radcial or a 5-membered oxaaryl, thiaaryl, oxazaaryl or thiaazaaryl radical which radicals optionally contain benzo and are optionally substituted by lower alkyl, lower alkoxy, lower-alkoxy carbonyl, carboxy, halogen, trifluoromethyl and/or nitro, especially corresponding pyridyl or quinolinyl, pyrimidinyl, furyl, benzofuryl, thienyl, benzothienyl, oxazolyl, benzoxazolyl, isoxazolyl, thiazolyl, benzthiazolyl or isothiazolyl, and $R_2$ represents hydrogen or lower alkyl.

The invention relates above all to compounds of the formula I in which Ph represents 1,2-phenylene which is optionally substituted by lower alkyl, for example methyl, lower alkoxy, for example methoxy, lower-alkoxy carbonyl, such as methoxycarbonyl, carboxy, halogen with an atomic number of up to 35, that is to say fluorine, chlorine or bromine, nitro or trifluoromethyl, X represents oxygen, $R_1$ denotes lower alkyl or a phenyl or phenyl-lower alkyl radical which are optionally substituted by lower alkyl, for example methyl, lower alkoxy, for example methoxy, lower-alkoxy carbonyl, such as methoxycarbonyl, carboxy, halogen with an atomic number of up to 35, that is to say fluorine, chlorine or bromine, trifluoromethyl and/or nitro, or pyridyl, for example 2- or 4-pyridyl, furyl, such as 2-furyl, thienyl, such as 2-thienyl, oxazolyl, for example 2-oxazolyl, isoxazolyl, for example 3-isoxazolyl, thiazolyl, for example 2-thiazolyl, or isothiazolyl, for example 3-isothiazolyl, which are optionally substituted by lower alkyl, for example methyl, and $R_2$ represents hydrogen or, to a lesser extent, represents lower alkyl, for example methyl.

The invention relates above all to compounds of the formula I in which Ph is 1,2-phenylene which can optionally be substituted by lower alkyl, for example methyl, lower alkoxy, for example methoxy, and/or halogen with an atomic number of up to 35, for example fluorine or chlorine, such substituents being, above all, in the 5-position and/or 6-position of the 2,3-dihydro-benzo[b]thiophene ring, X represents oxygen, $R_1$ denotes phenyl which is optionally substituted by lower alkyl, for example methyl, lower alkoxy, for example methoxy, and/or halogen with an atomic number of up to 35, for example fluorine or chlorine, or pyridyl, for example 2- or 4-pyridyl, furyl, such as 2-furyl, thienyl, such as 2-thienyl oxazolyl, for example 2-oxazolyl, isoxazolyl, for example 5-methyl-3-isoxazolyl, thiazolyl, for example 2-thiazolyl, or isothiazolyl, for example 3-isothiazolyl, which are optionally substituted by lower alkyl, for example methyl, and $R_2$ represents hydrogen.

The compounds of the present invention can be manufactured in a manner which is in itself known. Thus, they are obtained, for example, when a group of the formula $—C(=X)—N(R_1)(R_2)$ (Ia) is introduced into a compound of the formula

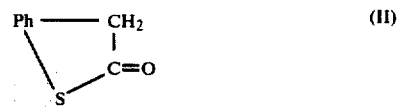

The 2-oxo-2,3-dihydro-benzo[b]thiophene starting material of the formula II can also be in the tautomeric form, that is to say in the form of the 2-hydroxy-benzo[b]thiophene compound.

The group of the formula Ia can be introduced direct or stepwise. Thus, this group can be introduced direct by reacting a compound of the formula II with a compound of the formula III

in which $R_o$ represents an etherified or esterified hydroxyl group or an optionally substituted amino group and $R_2^o$ has the meaning of $R_2$, or in which $R_o$ and $R_2^o$ conjointly form a bond.

An etherified hydroxyl group $R_o$ is preferably hydroxyl etherified by an optionally substituted hydrocarbon radical, such as lower alkyl, for example methyl or ethyl, or halogeno-lower alkyl, for example 2,2,2-trichloroethyl, and above all by optionally substituted phenyl, such as phenyl containing lower alkyl, lower alkoxy, halogen and/or nitro, and represents, for example, lower alkoxy, such as methoxy or ethoxy, halogeno-lower alkoxy, for example 2,2,2-trichloroethoxy, or phenoxy, whilst an esterified hydroxyl group is preferably esterified by a strong mineral acid and above all denotes halogen, especially chlorine. A substituted amino group contains as substituents one, and preferably two, optionally substituted hydrocarbon radicals, such as lower alkyl and/or phenyl which is optionally substituted, for example as indicated above, and represents, for example, lower alkylamino, such as methylamino or ethylamino, di-lower alkylamino, such as dimethylamino or diethylamino, or phenylamino and preferably diphenylamino, it being possible for the phenyl radical optionally to be substituted, for example by lower alkyl, such as methyl, lower alkoxy, for example methoxy, halogen, for example fluorine, chlorine or bromine, and/or nitro. A disubstituted amino group $R_o$ can, however, also represent a radical of the formula —N(R₁)(R₂).

The above reaction is usually carried out in the presence of a basic agent, such as a corresponding inorganic or organic agent. Inorganic bases which can be used are, above all, salt-forming agents and in particular agents which form alkali metal salts, such as alkali metal hydrides or alkali metal amides, as well as alkali metal-organic compounds, such as corresponding lower alkanolates, and also corresponding lower alkyl compounds or phenyl compounds, for example sodium methylate, sodium ethylate, potassium tert.-butylate, n-butyllithium or phenyl-lithium. Suitable organic bases are, above all, amines, such as tertiary amines, preferably tri-lower alkylamines, for example triethylamine, heterocyclic tertiary bases, especially of the pyridine types, fpr example pyridine, or quaternary bases, such as tetra-lower alkylammonium hydroxides or tri-lower alkyl-phenyl-lower alkylammonium hydroxides. In the presence of the base, the starting material of the formula II reacts in an anionic form, that is to say in the form of a salt, with the starting material of the formula III.

The starting materials are carbamic acid esters, carbamic acid halides, ureas and isocyanates which correspond to the formula III, as well as the corresponding sulphur compounds.

The reaction is carried out in the presence or absence of a solvent or diluent and, if necessary, with cooling or heating, for example in a temperature range of from about −10° C. to about +120° C., in a closed vessel and/or in an inert gas atmosphere, for example a nitrogen atmosphere.

The stepwise introduction of a group of the formula Ia into a starting material of the formula II can be carried out by reacting a compound of the formula II with a compound of the formula $R_o^b$—C(=X)—$R_o^a$ (IV), in which $R_o^a$ and $R_o^b$ independently of one another represent an etherified or esterified hydroxyl group, and treating a compound of the formula

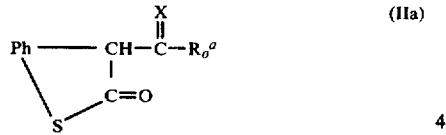

(IIa)

which is obtainable as an intermediate product, with an amine of the formula R₃—HN—R₂ (V).

Etherified or esterified hydroxyl groups $R_o^a$ and $R_o^b$ have, for example, the meanings indicated above for the corresponding radical $R_o$ and are, for example, lower alkoxy, such as methoxy or ethoxy, and also optionally substituted phenoxy, or halogen, for example chlorine. Suitable compounds of the formula IV are, for example, di-lower alkyl carbonates, for example diethyl carbonate or diphenyl carbonate, phosgene or lower alkyl halogenoformates, for example isobutyl chloroformate, as well as the corresponding compounds containing sulphur. The reaction of the starting material of the formula II with a compound of the formula IV is usually carried out in the presence of a base, such as one of those mentioned above, for example an alkali metal hydride or a trilower alkylamine. The intermediate product of the formula IIa is usually not isolated but is reacted direct with the amine of the formula V.

The above process steps are carried out in the absence or presence of a solvent or diluent and, if necessary, with cooling or heating, for example in a temperature range of from about −10° C. to about +120° C., in a closed vessel and/or in an inert gas atmosphere, for example a nitrogen atmosphere.

The starting materials are known or can be manufactured in a manner which is in itself known.

Starting materials of the formula II can be obtained, for example, when an enamine derived from a cyclohexanone which is optionally substituuted in the manner indicated for Ph is, in the presence of sulphur reacted with a cyanoacetic acid ester, the amino group of the resulting 2-amino-4,5,6,7-tetrahydrobenzothiophene-3-carboxylic acid ester is acylated, the reaction product is dehydrogenated with sulphur and the resulting 2-acylamino-benzothiophene-3-carboxylic acid ester is treated with sodium hydroxide solution, or when a corresponding benzothiophene is converted into the 2-lithium compound using butyl-lithium and this lithium compound is reacted with tributyl borate and the reaction product is oxidised with hydrogen peroxide. A process which is especially suitable for manufacturing compounds of the formula II which contain halogen substituents consists in converting a corresponding benzothiophene-2-carboxylic acid ester into the acid hydrazide using hydrazine, reacting this hydrazide with nitrous acid to give the azide, rearranging the latter to the isocyanate, converting the isocyanate into the urethane by alcoholysis, hydrolysing this urethane to the carbamic acid, decarboxylating the latter and hydrolysing the resulting 2-iminobenzothiophene.

Compounds of the formula III can be manufactured, for example, by reacting compounds of the formulae $R_o^b$—C(=X)—$R_o^a$ (IV) and HNR₁R₂ (V).

The new compounds can also be obtained when a compound of the formula

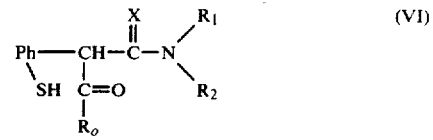

(VI)

in which R₁ represents an etherified or esterified hydroxyl group or an optionally substituted amino group, or a salt thereof, is subjected to cyclisation.

A salt of the starting material of the formula VI is, for example, an alkali metal salt.

A group $R_o$ can, for example, have the meaning indicated above and represents, for example, lower alkoxy, such as methoxy or ethoxy, halogeno-lower alkoxy, for example 2,2,2-trichloroethoxy, optionally substituted phenoxy or halogen, for example chlorine, and also represents lower alkylamino, for example methylamino, di-lower alkylamino, for example dimethylamino or diethylamino, phenylamino or diphenylamino, or a group of the formula —N(R₁)(R₂).

The above cyclisation reaction can be carried out in a manner which is in itself known, if necessary in the presence of a condensing agent, usually a basic condensing agent, such as a salt-forming agent, for example an agent which forms an alkali metal salt, inter alia including in the presence of an alkali metal lower alkanolate, for example sodium methylate, sodium ethylate or potassium tert.-butylate. The reaction is carried out in the absence or presence of a solvent or diluent, if necessary with cooling or warming, for example in a temperature range of from about 0° C. to about 150° C., in a closed vessel and/or in an inert gas atmosphere, for example a nitrogen atmosphere.

The starting materials of the formula VI can be manufactured in a manner which is in itself known, for example by introducing a group of the formulae —C(=O)—$R_o$ or —C(=X)—N($R_1$)($R_2$) into the methylene group in a benzyl unit of a compound of the formula $R_y$—S—Ph—$CH_2$—$R_x$ (VII), in which $R_x$ represents the radical of the formula —C(=X)—N($R_1$)($R_2$) (Ia) or the radical of the formula —C(=O)—$R_o$ and $R_y$ represents hydrogen or, preferably, a mercapto protective group, such as α-phenyl-lower alkyl which can be split off hydrogenolytically, for example benzyl, by reacting a compound of the formula VII with a suitable derivative of carbonic acid or thiocarbonic acid, such as a corresponding ester, for example a di-lower alkyl carbonate, such as diethyl carbonate, or diphenyl carbonate, a dihalide, for example phosgene or thiophosgene, a halogenoformic acid ester, for example a lower alkyl halogenoformate, urea or thiourea and also an isocyanate or isothiocyanate, usually in the presence of a basic agent, such as an alkali metal hydride, alkali metal amide or alkali metal lower alkanolate, or of an organic base, for example triethylamine. A mercapto protective group can then be split off in the customary manner, for example by treatment with catalytically activated hydrogen, and the mercapto group can thus be liberated.

The new compounds of the present invention can also be obtained when $R_z$ in a compound of the formula

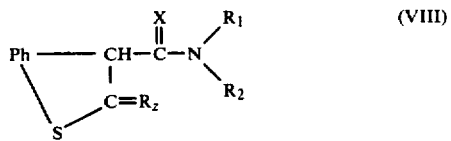

(VIII)

in which $R_z$ represents an optionally substituted imino group which can be converted into an oxo group by hydrolysis, is hydrolysed to oxo.

A substituent in a substituted imino group $R_z$ is, for example, an optionally substituted hydrocarbon radical, such as lower alkyl, for example methyl or ethyl, or phenyl, or an acyl group derived from a carboxylic acid or from a half-ester of carbonic acid, for example lower alkanoyl, such as acetyl, or benzoyl, or lower alkoxycarbonyl, such as methoxycarbonyl or ethoxycarbonyl.

The starting material of the formula VIII, which can also be in the tautomeric form of a corresponding 2-(H-$R_z$)-benzo[b]thiophene compound, in which the group —$R_z$—H represents an optionally monosubstituted amino group, is converted into the desired compound of the formula I by hydrolysis, preferably by treatment with water in the presence of a basic or acid agent, such as an inorganic base, for example an alkali metal hydroxide, or a mineral acid, for example hydrochloric acid or sulphuric acid.

The reaction is carried out in the presence or absence of a solvent or diluent and, if necessary, with cooling or heating, for example in a temperature range of from about −10° C. to about +120° C., in a closed vessel and/or in an inert gas atmosphere, for example a nitrogen atmosphere.

The starting material of the formula VIII can be manufactured in a manner which is in itself known when, for example, a compound of the formula

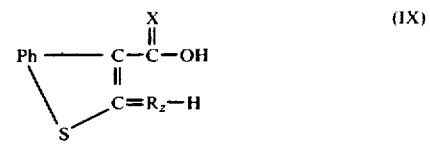

(IX)

in which $R_z$ preferably represents an unsubstituted imino group and the group —$R_z$—H therefore above all represents a primary amino group, is reacted with, for example, phosgene or a lower alkyl chloroformate and a compound of the formula

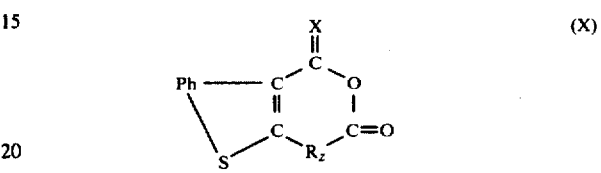

(X)

which is thus obtainable, is treated, optionally after introducing a substituent into a hydrogen-containing imino group $R_z$, for example by treatment with a lower alkyl halide in the presence of a reagent which forms an alkali metal compound, with an amine of the formula $R_1$—NH—$R_2$ (V) and, if desired, in a starting material of the formula VIII in which $R_z$ represents an unsubstituted imino group, or in a tautomer thereof in which —$R_z$—H represents an unsubstituted amino group, this imino group or amino group is substituted, for example by alkylation to introduce a lower alkyl group or by acylation, the latter being effected, for example, by treatment with a suitable symmetrical mixed or inner anhydride of a carboxylic acid.

The invention also relates to those embodiments of the process according to which a compound obtainable as an intermediate product at any stage of the process is used as the starting material and the missing process steps are carried out, or according to which a starting material is formed under the reaction conditions or is used in the form of a derivative thereof, optionally in the form of a salt.

The starting materials used for the process of the present invention are preferably those which lead to the compounds described initially as being particularly valuable.

The present invention also relates to pharmaceutical formulations which contain compounds of the formula I and to the use of these compounds, preferably in the form of pharmaceutical formulations. The pharmaceutical formulations according to the invention are those which are intended for enteral, such as oral, rectal or parenteral administration or for topical or local use on warmblooded animals and which contain the pharmacological active compound on its own or together with an excipient which can be used pharmaceutically. The dosage of the active compound depends on the species of warm-blooded animal, on the age and the state of health of the individual and on the mode of administration.

The new pharmaceutical formulations contain from about 10% up to about 95%, and preferably from about 20% up to about 90%, of the active compound. Pharmaceutical formulations according to the invention are, for example, those in the form of elixirs, aerosols or sprays or in the form of dosage units, such as dragees, tablets, capsules, suppositories or ampoules.

The pharmaceutical formulations of the present invention are manufactured in a manner which is in itself known, for example by means of conventional mixing, granulating, dragée-making, dissolving or lyophilising processes.

Formulations for oral use can be obtained, for example, by combining the active compound with solid excipients, optionally granulating a resulting mixture and processing the mixture or granules, after adding suitable auxiliaries if desired or necessary, to give tablets or dragée cores. Suitable excipients are, in particular, fillers, such as sugars, for example lactose or sucrose, mannitol or sorbitol, cellulose formulations and/or calcium phosphates, for example tricalcium phosphate or calcium hydrogen phosphate, as well as binders, such as starch pastes using, for example, maize starch, wheat starch, rice starch or potato starch, gelatine, tragacanth, methylcellulose, hydroxypropyl-methylcellulose, sodium carboxymethylcellulose and/or polyvinylpyrrolidone, and/or, if desired, disintegrating agents, such as the abovementioned starches, and also carboxymethylstarch, crosslinked polyvinylpyrrolidone, agar or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragée cores are provided with suitable coatings which, if desired, are resistant to gastric juices, and for this purpose, inter alia, concentrated sugar solutions, which optionally contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose formulations, such as acetylcellulose phthalate or hydroxypropylmethylcellulose phthalate, are used. Dyestuffs or pigments can be added to the tablets or dragée coatings, for example for identification or in order to characterise different doses of active compound.

Other pharmaceutical formulations which can be used orally are push-fit capsules made of gelatine, as well as soft, sealed capsules made of gelatine and a plasticiser, such as glycerol or sorbitol. The push-fit capsules can contain the active compound in the form of granules, for example mixed with fillers, such as lactose, binders, such as starches, and/or lubricants, such as talc or magnesium stearate, and, optionally, stabilisers. In soft capsules, the active compound is preferably dissolved or suspended in suitable liquids, such as fatty oils, liquid paraffin or liquid polyethylene glycols, it also being possible to add stabilisers.

Possible pharmaceutical formulations which can be used rectally are, for example, suppositories, which consist of a combination of the active compound with a suppository base. Suitable suppository bases are, for example, natural or synthetic triglycerides, paraffin hydrocarbons, polyethylene glycols or higher alkanols. In addition, it is also possible to use gelatine rectal capsules which consist of a combination of the active compound and a base; bases which can be used are, for example, liquid triglycerides, polyethylene glycols or paraffin hydrocarbons.

Suitable formulations for parenteral administration are, above all, aqueous solutions of an active compound in a water-soluble form, for example of a water-soluble salt, and also suspensions of the active compound, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and optionally also contain stabilisers.

Pharmaceutical formulations for topical and local use are, for example, for treatment of the skin, lotions and creams, which contain a liquid or semi-solid oil-in-water or water-in-oil emulsion, and ointments (these preferably containing a preservative), for treatment of the eyes, eye drops, which contain the active compound in aqueous or oily solution, and eye ointments, which preferably are produced in a sterile form, for treatment of the nose, powders, aerosols and sprays (similar to those described above for treatment of the respiratory passages) and also coarse powders which are administered by rapid inhalation through the nostrils, and nose drops, which contain the active compound in aqueous or oily solution, or, for local treatment of the mouth, boiled sweets for sucking, which contain the active compound in a composition which in general is formed from sugar and gum arabic or tragacanth and to which flavourings can be added, as well as pastilles, which contain the active compound in an inert composition, for example made of gelatine and glycerol or sugar and gum arabic.

The invention also comprises the use of the new compounds as pharmacologically active substances, and especially as anti-inflammatory agents, analgesics, uricosuric agents, anti-allergic agents and/or thrombolytic agents, preferably in the form of pharmaceutical formulations. The daily dose, which above all depends on the state of health of the organism to be treated and/or on the indication, is about 300 mg to about 1 g for a warm-blooded animal weighing about 70 kg.

The examples which follow illustrate the invention described above; however, they are in no way intended to restrict the scope of this invention. Temperatures are given in degrees centigrade.

EXAMPLE 1

A solution of 50 g of 2,3-dihydro-2-oxo-benzo[b]thiophene in 200 ml of hexamethylphosphoric acid triamide is added dropwise to a suspension of 16 g of a 50% strength sodium hydride/mineral oil dispersion in 500 ml of hexamethylphosphoric acid triamide, whilst cooling, the temperature being kept below 15°. After stirring for one hour at room temperature, 77 g of phenyl N-(2-fluorophenyl)-carbamate are added in portions, with external cooling. The reaction mixture is stirred for a further 16 hours at room temperature and poured into a mixture of 300 ml of 2 N hydrochloric acid and 3,000 ml of ice water. An oil separates out and this crystallises after about 2 hours. The crystalline product, in which solvent is incorporated, is dissolved in 1,000 ml of diethyl ether and the solution is washed with water. The organic phase is separated off, dried over sodium sulphate and evaporated to dryness. The crude product is recrystallised from diethyl ether and gives N-(2-fluorophenyl)-2-oxo-2,3-dihydro-3-benzo[b]thiophenecarboxamide, melting point 155°-156°.

EXAMPLE 2

N-(2,4-Difluorophenyl)-2-oxo-3,2-dihydro-3-benzo[b]thiophenecarboxamide, melting point 158°-161°

(after recrystallisation from isopropanol/petroleum ether) is obtained in a manner analogous to that described in Example 1, the starting materials used being 10 g of 2,3-dihydro-2-oxo-benzo[b]thiophene and 16.6 g of phenyl N-(2,4-difluorophenyl)-carbamate.

EXAMPLE 3

The following compounds are obtained in a manner analogous to that described in Example 1 and these compounds are obtained from the reaction as a crude crystalline product in which no solvent is incorporated and which can be recrystallised direct: N-(2-chlorophenyl)-2-oxo-2,3-dihydro-3-benzo[b]thiophenecarboxamide, melting point 167°–169° (after recrystallisation from isopropanol; using 12 g of 2,3-dihydro-2-oxo-benzo[b]thiophene and 19.2 g of phenyl N-(2-chlorophenyl)-carbamate as the starting materials), N-(4-fluorophenyl)-2-oxo-2,3-dihydro-3-benzo[b]thiophenecarboxamide, melting point 169°–170° (after recrystallisation from diethyl ether; using 10 g of 2,3-dihydro-2-oxo-benzo[b]thiophene and 15.4 g of phenyl N-(4-fluorophenyl)-carbamate as the starting materials), N-(4-chlorophenyl)-2-oxo-2,3-dihydro-3-benzo[b]thiophenecarboxamide, melting point 159°–161° (after recrystallisation from a mixture of methanol and water; using 10 g of 2,3-dihydro-2-oxo-benzo[b]thiophene and 16.5 g of phenyl N-(4-chlorophenyl)-carbamate as the starting materials), N-phenyl-2-oxo-2,3-dihydro-3-benzo[b]thiophenecarboxamide, melting point 146°–147° (after recrystallisation from a mixture of methanol and water; using 10 g of 2,3-dihydro-2-oxo-benzo[b]thiophene and 14.2 g of phenyl N-phenyl-carbamate as the starting materials) and N-(2-thiazolyl)-2-oxo-2,3-dihydro-3-benzo[b]thiophenylcarboxamide, melting point 288° (after recrystallisation from a mixture of dimethylformamide and water; using 7.5 g of 2,3-dihydro-2-oxo-benzo[b]thiophene and 11 g of phenyl-N-(2-thiazolyl)-carbamate as the starting materials).

EXAMPLE 4

10 g of 2,3-dihydro-2-oxo-benzo[b]thiophene and 14.3 g of phenyl N-(2-pyridyl)-carbamate are reacted in a manner analogous to that described in Example 1. After stirring the reaction mixture for 16 hours at room temperature and pouring into the hydrochloric acid/water mixture, a brown-violet precipitate is obtained and this is filtered off and boiled thoroughly in 3,000 ml of acetone, under reflux. The crystalline material which has not dissolved is filtered off and the filtrate is concentrated to a volume of about 300 ml. The material which has crystallised out in the cold is identical with the first crystalline product. N-(2-Pyridyl)-2-oxo-2,3-dihydro-3-benzo[b]thiophenecarboxamide, which is thus obtainable, melts at above 280°.

EXAMPLE 5

A solution of 18.2 g of 2,3-dihydro-2-oxo-benzo[b]thiophene in 60 ml of hexamethylphosphoric acid triamide is added dropwise to a suspension of 5.9 g of a 50% strength sodium hydride/mineral oil suspension in 180 ml of hexamethylphosphoric acid triamide whilst cooling, the reaction temperature being kept below 15°. After stirring for one hour at room temperature, 30.4 g of phenyl N-(3-chlorophenyl)-carbamate are added in portions, with external cooling. The mixture is stirred for a further 16 hours at room temperature and poured onto a mixture of 100 ml of 2 N hydrochloric acid and 1,000 g of ice, whereupon an oil separates out; this oil crystallises on leaving to stand for several hours. The crystals are collected and dissolved in 300 ml of diethyl ether. The solution is washed with water and the organic phase is separated off, dried over sodium sulphate and evaporated to dryness. The residue is recrystallised from ether and gives N-(3-chlorophenyl)-2-oxo-2,3-dihydro-3-benzo[b]thiophenecarboxamide with a melting point of 175°–177°.

EXAMPLE 6

2 ml of morpholine are added to a boiling suspension of 7 g of N-(3-chlorophenyl)-2-oxo-2,3-dihydro-3-benzo[b]thiophenecarboxamide in 200 ml of acetone, whereupon everything goes into solution. The solution, which is now clear, is cooled and diluted with 250 ml of petroleum ether and the morpholine salt of N-(3-chlorophenyl)-2-oxo-2,3-dihydro-3-benzo[b]thiophenecarboxamide crystallises out and is filtered off and dried. It melts at 172.5°–173.5°.

EXAMPLE 7

2.2 g of N-(3-chlorophenyl)-2-oxo-2,3-dihydro-3-benzo[b]thiophenecarboxamide are warmed gently in a mixture of 7.5 ml of N sodium hydroxide solution and 30 ml of water and everything goes into solution at about 50°. A solution of 1.1 g of zinc sulphate heptahydrate in 5 ml of water is added and after about 30 minutes the crystalline precipitate consisting of the zinc salt of N-(3-chlorophenyl)-2-oxo-2,3-dihydro-3-benzo[b]thiophene-carboxamide is filtered off and dried. The salt melts at about 172° (with evolution of gas).

EXAMPLE 8

A solution of 6 g of 2,3-dihydro-2-oxo-benzo[b]thiophene in 40 ml of tetrahydrofuran is added dropwise, at 10° to 20°, to a stirred suspension of 1.93 g of a 50% strength sodium hydride/mineral oil suspension in 50 ml of tetrahydrofurane. The mixture is stirred for a further 30 minutes at room temperature and 5.5 g of 3-fluorophenyl isocyanate are then added slowly dropwise, an exothermic reaction taking place. The reaction mixture is then stirred for a further one hour at room temperature and for one hour at 40° and is poured into a mixture of 500 ml of ice water and 50 ml of 2 N hydrochloric acid and the precipitate, which at first is oily but immediately crystallises, is filtered off and recrystallised from acetone/petroleum ether. N-(3-Fluorophenyl)-2-oxo-2,3-dihydro-3-benzo[b]thiophenecarboxamide with a melting point of 169°–171° is obtained.

EXAMPLE 9

20 g of N-(3-chlorophenyl)-2-oxo-2,3-dihydro-3-benzo[b]thiophene-carboxamide are suspended in 250 ml of acetone and 66 ml of N sodium hydroxide solution are added, whereupon a solution forms. The solution is evaporated to dryness and the evaporation residue is stirred first with toluene and then with diethyl ether, filtered off and dried. This gives the sodium salt of N-(3-chlorophenyl)-2-oxo-2,3-dihydro-3-benzo[b]thiophenecarboxamide, melting point > 255°.

EXAMPLE 10

Further compounds obtained in a manner analogous to that described in Example 1 are: N-(2,4-dichlorophenyl)-2-oxo-2,3-dihydro-3-benzo[b]thiophenecarboxamide, melting point 201°–203° (using 12 g of 2,3-dihydro-2-oxo-benzo[b]thiophene and 22.5 g of phenyl N-(2,4-dichlorophenyl)-carbamate as the starting materials), N-(4-methoxyphenyl)-2-oxo-2,3-dihydro-3-benzo[b]thiophenecarboxamide, melting point 181°–183° (using 12 g of 2,3-dihydro-2-oxo-benzo[b]thiophene and 19.4 g of phenyl N-(4-methoxyphenyl)-carbamate as the starting materials), N-(2-methylphenyl)-2-oxo-2,3-dihydro-3-benzo[b]thiophenecarboxamide, melting point 153°–155° (using 12 g of 2,3-dihydro-2-oxo-benzo[b]thiophene and 18.1 g of phenyl N-(2-methylphenyl)-carbamate as the starting materials), N-(3,5-bistrifluoromethylphenyl)-2-oxo-2,3-dihydro-3-benzo[b]thiophenecarboxamide, melting point 169°–171° (using 7.5 g of 2,3-dihydro-2-oxo-benzo[b]thiophene and 17.5 g of phenyl N-(3,5-bis-trifluorophenyl)-carbamate as the starting materials), N-(4-methylphenyl)-2-oxo-2,3-dihydro-3-benzo[b]thiophenecarboxamide, melting point 176°–179° (using 12 g of 2,3-dihydro-2-oxo-benzo[b]thiophene and 18.1 g of phenyl N-(4-methylphenyl)-carbamate as the starting materials), N-(4-ethoxyphenyl)-2-oxo-2,3-dihydro-3-benzo[b]thiophene-carboxamide, melting point 149°–151° (using 20.5 g of phenyl N-(4-ethoxyphenyl)-carbamate and 12 g of 2,3-dihydro-2-oxo-benzo[b]thiophene as the starting materials), N-(4-bromophenyl)-2-oxo-2,3-dihydro-3-benzo[b]thiophenecarboxamide, melting point 178°–180° (using 7.5 g of 2,3-dihydro-2-oxo-benzo[b]thiophene and 14.6 g of phenyl N-(4-bromophenyl)-carbamate as the starting materials), N-(3,4-dimethoxyphenyl)-2-oxo-2,3-dihydro-3-benzo[b]thiophenecarboxamide, melting point 194°–196° (using 12 g of 2,3-dihydro-2-oxo-benzo[b]thiophene and 21.8 g of phenyl N-(3,4-dimethoxyphenyl)-carbamic as the starting materials), N-(2-methoxyphenyl)-2-oxo-2,3-dihydro-3-benzo[b]thiophenecarboxamide, melting point 140°–142° (using 12 g of 2,3-dihydro-2-oxo-benzo[b]thiophene and 19.5 g of phenyl N-(2-methoxyphenyl)-carbamate as the starting materials), N-[3-(5-methylisoxazolyl)]-2-oxo-2,3-dihydro-3-benzo[b]thiophene-carboxamide, m.p. 194° to 196°, N-(2-methoxycarbonylphenyl)-2-oxo-2,3-dihydro-3-benzo[b]thiophene-carboxamide, m.p. 147° to 149° and, by its hydrolysis, N-(2-carboxyphenyl)-2-carboxyphenyl)-2-oxo-2,3-dihydro-2-benzo[b]thiophene-carboxamide and N-(3,4-dichlorophenyl)-2-oxo-2,3-dihydro-3-benzo[b]thiophenecarboxamide, melting point 192°–194° (using 17.9 g or 2,3-dihydro-2-oxo-benzo[b]thiophene and 16.9 g of phenyl N-(3,4-dichlorophenyl)-carbamate as the starting materials).

EXAMPLE 11

470 mg (2.11 mmols) of ethyl 2-oxo-2,3-dihydro-3-benzo[b]thiophene-carboxylate and 206 mg (2.22 mmols) of aniline in 3 ml of xylene are boiled under reflux for 5 hours. After cooling, the product is precipitated by adding hexane (3 ml). After further dilution with 5 ml of ether and stirring, crystalline N-phenyl-2-oxo-2,3-dihydro-3-benzo[b]thiophene-carboxamide with a melting point of 140°–142° is obtained and filtered off.

In analogous manner, also N-butyl-2,3-dihydro-2-oxo-3-benzo[b]thiophene-carboxamide and N-benzyl-2,3-dihydro-2-oxo-3-benzo[b]thiophene-carboxamide can be manufactured.

EXAMPLE 12

1.63 g of sodium hydride (5% strength suspension) are added to a solution, which has been cooled to 5°, of 6.0 g (32.5 mmols) of 5-chloro-2,3-dihydro-2-oxo-benzo[b]thiophene in 75 ml of hexamethylphosphoric acid triamide and the mixture is stirred until the evolution of hydrogen has ceased (about 10 minutes). The cooling bath is removed and the mixture is stirred for a further one hour at room temperature. After cooling again, 8.43 g of phenyl N-(3-chlorophenyl)carbamate are added in portions. After the addition is complete, the batch is left at room temperature for one hour, introduced into a mixture of 1 l of ice water and 20 ml of 2 N hydrochloric acid and extracted with twice 300 ml of ethyl acetate. The combined extracts are washed three times with water and dried over magnesium sulphate. After concentrating in vacuo, a crystalline residue of N-(3-chlorophenyl)-5-chloro-2,3-dihydro-2-oxo-3-benzo[b]-thiophene-carboxamide is obtained. This is washed with 100 ml of ether/hexane (1:1) and then with hexane and dried in vacuo. Virtually colourless crystals with a melting point of 160°–163° are obtained.

In an analogous manner, N-(2-thiazolyl)-5-chloro-2,3-dihydro-2-oxo-3-benzo[b]thiophene-carboxamide, m.p. 296°–9°, and N-phenyl-5-chloro-2,3-dihydro-2-oxo-3-benzo[b]thiophenecarboxamide, m.p. 170°–2°, are obtained.

5-Chloro-2,3-dihydro-benzo[b]thiophene, which is used as the starting material, can be prepared as follows:

8.00 g (35.3 mmols) of 5-chloro-2-benzo[b]thiophenecarboxylic acid methyl ester and 10 ml of hydrazine hydrate in 100 ml of absolute ethanol are boiled under reflux for 45 minutes. The cooled suspension is diluted with 100 ml of ice water and the product is filtered off. It is washed with two 40 ml portions of methanol and dried in vacuo. 5-Chloro-2-benzo[b]thiophene-carboxylic acid hydrazide with a melting point of 254°–255° is obtained.

A solution of 2.51 g of sodium nitrite in 5 ml of water is added dropwise to a suspension, which has been cooled to 15°, of 7.5 g (33.1 mmols) of 5-chloro-2-benzo[b]thiophenecarboxylic acid hydrazide in 100 ml of glacial acetic acid, whilst stirring. In order to achieve complete solution, a further 100 ml of glacial acetic acid are added. The mixture is then stirred thoroughly for 15 minutes at room temperature and subsequently 500 ml of ice water are added. The 5-chloro-2-benzo[b]thiophene-carboxylic acid azide which has precipitated is filtered off and washed thoroughly with ice water and a solution of this azide in 200 ml of methylene chloride is dried over magnesium sulphate, after separating off the aqueous layer. After stripping off the solvent in vacuo at 20°, a residue of yellowish crystals with a melting point of 90°–91° is obtained.

7.0 g (28.3 mmols) of 5-chloro-2-benzo[b]thiophenecarboxylic acid azide are dissolved in 15 ml of absolute alcohol and the solution is boiled under reflux for 6 hours. After concentrating the solution in vacuo and recrystallising the residue from 30 ml of methanol, 2-ethoxycarbonylamino-5-chloro-benzo[b]thiophene is obtained in the form of brownish crystals with a melting point of 133°–135°. Further product can be obtained from the mother liquor residue by chromatography on silica gel and elution with benzene.

A mixture of 37.1 g (145.2 mmols) of 2-ethoxycarbonylamino-5-chloro-benzo[b]thiophene, 300 ml of glacial acetic acid, 50 ml of water and 50 ml of concentrated sulphuric acid is boiled under reflux for 75 minutes. The cooled reaction solution is poured into 5 l of ice water and 5-chloro-2,3-dihydro-2-oxo-benzo[b]thiophene precipitate as crystals. It is filtered off and washed well with water. The moist crude product is dissolved in 300 ml of methylene chloride and the solution is dried over magnesium sulphate and concentrated. For further purification, the product is dissolved in 200 ml of benzene/hexane (1:1) and the solution is passed through a column containing 300 g of silica gel. The residue obtained by concentrating the eluate in vacuo consists of pure product: colourless crystals with a melting point of 113°–114°.

EXAMPLE 13

A solution of 6.0 g of 5-chloro-2,3-dihydro-2-oxobenzo[b]thiophene and 1.63 g of sodium hydride in 75 ml of hexamethylphosphoric acid triamide is prepared as described in Example 12. 8.76 g (34.1 mmols) of phenyl N-(4-ethoxyphenyl)-carbamate are added in portions to this solution and the reaction mixture is stirred for 3 hours. Working up is also carried out as indicated in Example 12 and crude N-(4-ethoxyphenyl)-5-chloro-2,3-dihydro-2-oxo-3-benzo[b]thiophenecarboxamide is obtained. When recrystallised from acetone, this melts at 202°–205°.

EXAMPLE 14

A solution of 6.0 g of 5-chloro-2,3-dihydro-2-oxobenzo[b]thiophene and 1.63 g of sodium hydride in 75 ml of hexamethylphosphoric acid triamide is prepared as described in Example 12. 7.88 g of phenyl N-(2-fluorophenyl)-carbamate are added in portions to this solution and the reaction mixture is stirred for 3 hours. The procedure employed for working up is as indicated in Example 12, sodium chloride solution being added to the aqueous layer during the extraction with ethyl acetate in order to achieve better phase separation. On concentrating the organic layer in vacuo to a small volume, N-(2-fluorophenyl)-5-chloro-2,3-dihydro-2-oxo-3-benzo[b]thiophenecarboxamide precipitates in the form of crystals with a melting point of 205°–207°. It is filtered off, washed with cold ethyl acetate and hexane and dried. Further product can be obtained from the mother liquors.

EXAMPLE 15

Tablets containing 0.1 g of N-(2-fluorophenyl)-2-oxo-2,3-dihydro-3-benzo[b]thiophenecarboxamide are prepared as follows:

| Composition (for 1,000 tablets): | |
|---|---|
| N-(2-fluorophenyl)-2-oxo-2,3-dihydro-3-benzo[b]thiophenecarboxamide | 100.00 g |
| lactose | 50.00 g |
| wheat starch | 73.00 g |
| colloidal silica | 13.00 g |
| magnesium stearate | 2.00 g |
| talc | 12.00 g |
| water | q.s. |

The N-(2-fluorophenyl)-2-oxo-2,3-dihydro-3-benzo[b]thiophenecarboxamide is mixed with part of the wheat starch and with the lactose and the colloidal silica and the mixture is forced through a sieve. A further part of the wheat starch is mixed to a paste with five times the amount of water on a water bath and the above pulverulent mixture is kneaded with this paste until a slightly plastic mass has formed. The plastic mass is pressed through a sieve which has a mesh width of about 3 mm and dried and the dry granules are again forced through a sieve. The remaining wheat starch, the talc and the magnesium stearate are then mixed in and the resulting mixture is pressed to give tablets weighing 0.25 g.

Tablets which each contain 0.1 g of the other N-phenyl-2-oxo-2,3-dihydro-3-benzo[b]thiophene-carboxamides mentioned in Example 1-14, and in particular which contain 0.1 g of N-(4-ethoxyphenyl)-5-chloro-2-oxo-2,3-dihydro-3-benzo[b]thiophenecarboxamide, N-(4-fluorophenyl)-2-oxo-2,3-dihydro-3-benzo[b]thiophene-carboxamide, N-(2,4-difluorophenyl)-2-oxo-2,3-dihydro-3-benzo[b]thiophene-carboxamide, N-(3-fluorophenyl)-2-oxo-2,3-dihydro-3-benzo[b]thiophenecarboxamide, N-(2-fluorophenyl)-5-chloro-2-oxo-2,3-dihydro-3-benzo[b]thiophenecarboxamide or N-(3-chlorophenyl)-2-oxo-2,3-dihydro-3-benzo[b]thiophene-carboxamide, or their sodium, zinc or morpholine salts, can be prepared in an analogous manner.

EXAMPLE 16

In an analogous manner as described in Example 1, N-phenyl-5-carboxy-2,3-dihydro-2-oxo-3-benzo[b]thiophene-carboxamide, N-(2-methylphenyl)-5-carboxy-2,3-dihydro-2-oxo-3-benzo[b]thiophene-carboxamide, N-(2-chlorophenyl)-5-carboxy-2,3-dihydro-2-oxo-3-benzo[b]thiophene-carboxamide and N-(3-chlorophenyl)-5-carboxy-2,3-dihydro-2-oxo-3-benzo[b]thiophene-carboxamide, as well as their lower alkyl esters, especially methyl esters, can be manufactured starting from 5-carboxy-2,3-dihydro-2-oxobenzo[b]thiophene or 5-methoxycarbonyl-2,3-dihydro-2-oxo-benzo[b]thiophene respectively.

The starting materials can be prepared from 3-methyl-4-nitro-benzoic acid ethyl ester by bromiation of the methyl group, reacting of the resulting 3-bromomethyl-4-nitro-benzoic acid ethyl ester with potassium cyanide and subsequently with benzylmercaptane to yield 3-cyanomethyl-4-benzylmercapto-benzoic acid ethyl ester which is then hydrolysed under ring-closure yielding 5-carboxy-2,3-dihydro-2-oxo-benzo[b]thiophene, the carboxy group of which can then be esterified, if required.

EXAMPLE 17

In an analogous manner as described in Example 12, N-(2-fluorophenyl)-6-chloro-2,3-dihydro-2-oxo-3-benzo[b]thiophenecarboxamide, m.p. 187° to 190°, N-phenyl-6-chloro-2,3-dihydro-2-oxo-3-benzo[b]thiophene-carboxamide, m.p. 201° to 204°, N-(3-chlorophenyl)-6-chloro-2,3-dihydro-2-oxo-3-benzo[b]thiophenecarboxamide, m.p. 212° to 215°, and N-(2-chlorophenyl)-6-chloro-2,3-dihydro-2-oxo-3-benzo[b]thiophene-carboxamide, m.p. 169° to 170°, can be manufactured starting from 6-chloro-2-benzo[b]thiophene-carboxylic acid hydrazide which can be prepared reacting the corresponding ethyl or methyl ester with hydrazine.

EXAMPLE 18

In an analogous manner as described in Example 12, N-phenyl-2,3-dihydro-6-methoxy-2-oxo-3-benzo[b]thiophene-carboxamide, N-(2-chlorophenyl)-2,3-dihydro-6-methoxy-2-oxo-3-benzo[b]thiophene-carboxamide, N-(3-chlorophenyl)-2,3-dihydro-6-methoxy-2-oxo-3-benzo[b]thiophene-carboxamide and N-(2-fluorophenyl)-2,3-dihydro-6-methoxy-2-oxo-3-benzo[b]thiophene-carboxamide can be manufactured from 6-methoxy-2-benzo[b]thiophene-carboxylic acid hydrazide which can be prepared by reductive de-halogenation of 3-chloro-6-methoxy-2-benzo[b]thiophene-carboxylic acid methyl ester and subsequent reaction with hydrazine. Analogously, N-phenyl-2,3-dihydro-5-nitro-2-oxo-3-benzo[b]thiophene-carboxamide, N-(2-chlorophenyl)-2,3-dihydro-5-nitro-2-oxo-3-benzo[b]thiophene-carboxamide, N-(3-chlorophenyl)-2,3-dihydro-5-nitro-2-oxo-3-benzo[b]thiophene-carboxamide and N-(2-fluorophenyl)-2,3-dihydro-5-nitro-2-oxo-3-benzo[b]thiophene-carboxamide can be manufactured from 5-nitro-2-benzo[b]thiophene-carboxylic acid hydrazide, obtained from the methyl ester and hydrazine.

We claim:

1. An oxothia compound of the formula

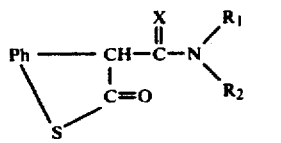

in which Ph represents 1,2-phenylene or 1,2-phenylene which is substituted by lower alkyl, lower alkoxy, halogen, trifluoromethyl and/or nitro, X represents oxygen or sulphur, $R_1$ represents lower alkyl, lower alkenyl, cycloalkyl, cycloalkenyl cycloalkyl-lower alkyl, phenyl-lower alkyl or phenyl-lower alkyl which is substituted in the phenyl part by lower alkyl, lower alkoxy, halogen, trifluoromethyl and/or nitro, phenyl or phenyl which is substituted by lower alkyl, lower alkoxy, halogen, trifluoromethyl and/or nitro, and $R_2$ represents hydrogen or lower alkyl, or a pharmaceutically acceptable salt thereof.

2. A compound of the formula I as claimed in claim 1, in which Ph represents 1,2-phenylene which is optionally substituted by lower alkyl, lower alkoxy, halogen with an atomic number of up to 35 or trifluoromethyl, X represents oxygen, $R_1$ denotes phenyl which is optionally substituted by lower alkyl, lower alkoxy, halogen with an atomic number of up to 35, trifluoromethyl and/or nitro, and $R_2$ represents hydrogen or lower alkyl, or a pharmaceutically acceptable salt thereof.

3. A compound of the formula I as claimed in claim 1, in which Ph represents 1,2-phenylene which can optionally be substituted by lower alkyl, lower alkoxy and/or halogen with an atomic number of up to 35, X represents oxygen, $R_1$ denotes phenyl which is optionally substituted by lower alkyl, lower alkoxy and/or halogen with an atomic number of up to 35, and $R_2$ represents hydrogen.

4. A compound as claimed in claim 1 and being the N-(3-chlorophenyl)-2-oxo-2,3-dihydro-3-benzo[b]thiophenecarboxamide or a pharmaceutically acceptable salt thereof with a base.

5. A compound as claimed in claim 1 and being the N-(3-chlorophenyl)-5-chloro-2-oxo-2,3-dihydro-3-benzo[b]thiophenecarboxamide or a pharmaceutically acceptable salt thereof with a base.

6. A compound as claimed in claim 1 and being the N-(2-fluorophenyl)-2-oxo-2,3-dihydro-3-benzo[b]thiophenecarboxamide or a pharmaceutically acceptable salt thereof with a base.

7. A compound as claimed in claim 1 and being the N-phenyl-6-chloro-2-oxo-2,3-dihydro-3-benzo[b]thiophene-carboxamide or a pharmaceutically acceptable salt thereof with a base.

8. A compound as claimed in claim 1 and being the N-(3-chlorophenyl)-6-chloro-2-oxo-2,3-dihydro-3-benzo[b]thiophene-carboxamide or a pharmaceutically acceptable salt thereof with a base.

9. A compound as claimed in claim 1 and being the N-(2-fluorophenyl)-6-chloro-2-oxo-2,3-dihydro-3-benzo[b]thiophene-carboxamide or a pharmaceutically acceptable salt thereof with a base.

* * * * *